(12) United States Patent
Petrie, Jr.

(10) Patent No.: US 9,718,003 B1
(45) Date of Patent: Aug. 1, 2017

(54) CENTRIFUGE TUBE ASSEMBLY AND METHOD OF USING THE SAME

(71) Applicant: Thomas R. Petrie, Jr., Hamburg, NJ (US)

(72) Inventor: Thomas R. Petrie, Jr., Hamburg, NJ (US)

(73) Assignee: CELLMEDIX HOLDINGS, LLC, Franklin, NJ (US)

( * ) Notice: Subject to any disclaimer, the term of this patent is extended or adjusted under 35 U.S.C. 154(b) by 363 days.

(21) Appl. No.: 14/680,707

(22) Filed: Apr. 7, 2015

(51) Int. Cl.
*G01N 9/30* (2006.01)
*B01D 17/02* (2006.01)
*C12N 5/071* (2010.01)
*B01L 3/00* (2006.01)

(52) U.S. Cl.
CPC ....... *B01D 17/0217* (2013.01); *C12N 5/0602* (2013.01); *B01L 3/502* (2013.01); *B01L 3/5021* (2013.01)

(58) Field of Classification Search
None
See application file for complete search history.

(56) References Cited

U.S. PATENT DOCUMENTS

| | | | |
|---|---|---|---|
| 6,835,353 B2 | 12/2004 | Smith et al. | |
| 7,179,391 B2 | 2/2007 | Leach et al. | |
| 7,829,022 B1 * | 11/2010 | Lich | B01L 3/502 210/645 |
| 7,976,797 B2 | 7/2011 | Chun | |

* cited by examiner

*Primary Examiner* — Jill Warden
*Assistant Examiner* — Julie Tavares
(74) *Attorney, Agent, or Firm* — Dennis L. Thomte; Thomte Patent Law Office LLC (57) ABSTRACT

A centrifuge tube assembly which allows for a single centrifuge cycle and which permits the aspiration of fluids from multiple levels with the centrifuge tube assembly. A modified centrifuge assembly is described wherein the inner tube has an externally threaded portion at its upper end. The method of using the centrifuge tube assembly is also described wherein the centrifuge tube assembly may be used for the aspiration, separation, isolation and extracting of discrete layer in a liquid suspension.

6 Claims, 13 Drawing Sheets

CENTRIFUGE TUBE ASSEMBLY AND METHOD OF USING THE SAME

BACKGROUND OF THE INVENTION

Field of the Invention

This invention relates to an improved centrifuge tube assembly which allows for a single centrifugation cycle and the aspiration of fluids from multiple levels within the centrifuge tube assembly. More particularly, the device may be used for the aspiration, separation, isolation and extraction of discrete layers in a liquid suspension.

Description of the Related Art

Various medical procedures utilize platelet-rich blood plasma. The blood product is effective due to its growth promoting features, which are proven to assist greatly in wound healing and bone regeneration. Over the last decade, many devices have been developed which allow a clinician to isolate and concentrate the platelet component from a whole blood sample including that described in U.S. Pat. No. 7,829,022 which uses a dual centrifugal cycle process. Alternate devices have been developed which employ a single centrifugation cycle including that described in U.S. Pat. Nos. 7,976,796 and 7,179,391.

Although the devices of the above-identified patents have experienced some commercial success, it is believed that the devices have certain drawbacks or disadvantages. For example, none of the prior art devices are capable of collecting the target fluid (platelet rich plasma) with a single aspiration after a single centrifugation cycle. Further, none of the prior art devices have an integrated locking mechanism to secure the inner tube at any targeted component locations from 15 ml to 40 ml. None of the prior art devices incorporate an O-ring to introduce a tactical feedback, similar to the dispense/aspirating action of a syringe, and containment seal. The tubes of U.S. Pat. Nos. 7,976,796 and 7,179,391 are prone to kinking. The device of this invention eliminates the utilization of the integral flexible tube employed in U.S. Pat. Nos. 7,976,796 and 7,179,391. The device of this invention eliminates the need for a second spin requirement employed in U.S. Pat. No. 7,829,022. The feature of the instant invention which is not found in the listed US Patents is a manual adjust aspiration tube to visually align the target layer of choice. The device of this invention features an aspiration tube design that has a dimensional relationship between the visual indicator and aspiration port to maintain an RBC and Buffy coat ratio that allows a range of volume choices. The device of this invention eliminates the need to remove or isolate the RBC prior to PRP aspiration, a feature not found in other PRP devices. The device of this invention allows a min/max PRP volume selection from 3 ml to 30 ml, a feature not found in other devices. The device of this invention integrates a single centrifugation, a single aspiration, a single syringe and a single biohazard disposable to deliver an end product, which is not possible in any prior art device.

SUMMARY OF THE INVENTION

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

A centrifuge tube assembly is disclosed which includes an elongated and vertically disposed outer containment tube having an open upper end and a closed lower end. The outer containment tube is comprised of a transparent material. The outer containment tube has a vertically disposed cylindrical post centrally positioned therein at the lower end thereof with the post extending upwardly from the lower end of the outer containment tube. The cylindrical post has an elongated and vertically disposed keyway formed therein which extends inwardly thereinto between the lower and the upper ends thereof.

The centrifuge tube assembly also includes an elongated and vertically disposed inner tube, having an open lower end and an open upper end which is positioned in the outer containment tube. The lower end of the inner tube is vertically slidably mounted on the cylindrical post. The inner tube has an alignment key therein at its lower end which is slidably received by the keyway in the cylindrical post to prevent rotation of the inner tube with respect to the cylindrical post and the outer containment tube.

The inner tube has an aspiration port formed therein above the lower end and has an imprinted band thereon above the aspiration port. The outer tube also has an imprinted 50 mm line thereon below the upper end thereof. A cup-shaped cap is selectively removably mounted on the upper end of the outer containment tube. The cup-shaped cap has a filtered vent port which is in communication with the upper interior containment tube. The inner tube is selectively slidably extended upwardly through the cap whereby the upper end of the inner tube is positioned above the cap. A seal means is provided in the cap between the cap and the inner tube to prevent fluids from passing outwardly from the interior of the outer containment tube around the inner tube.

A locking assembly is associated with the cap for selectively locking the inner tube in various vertical positions with respect to the outer containment tube. The upper end of the inner tube has a male luer thereon. A female luer cap is provided for selective engagement with the male luer to close the male luer.

A modified form of the centrifuge assembly is also described. The method of using the centrifuge tube assembly is also described.

It is therefore a principal object of the invention to provide an improved centrifuge tube assembly and the method of using the same.

A further object of the invention is to provide a device of the type described wherein the device may serve both as a collection vessel and a tube for the centrifugation of fluids into their discreet components.

A further object of the invention is to provide a device of the type described which includes a single port at the top of the device which may be used to fill and aspirate fluid, pre-centrifugation and post-centrifugation therefrom.

Yet another object of the invention is to provide a device of the type described wherein the clinician has complete control over the concentration and volume of the end product.

Still another object of the invention is to provide a centrifuge device assembly which may be used with any centrifuge machine capable of at least 1900 rcf and 85-50 ml swing out rotor.

A further object of the invention is to provide a centrifuge tube assembly of the type described which provides the most cost effective solution specifically designed for the concentration of platelets, stem cells or adipose tissue.

A further object of the invention is to provide a centrifuge tube assembly having the ability to extract the blood component of choice after centrifugation.

A further object of the invention is to provide a centrifuge tube assembly in which the surfaces that interface with blood are constructed of a plastic material that is slippery and prevents the adhesion of platelets or other cells.

These and other objects will be apparent to those skilled in the art.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DESCRIPTION OF THE PREFERRED EMBODIMENT

Embodiments are described more fully below with reference to the accompanying figures, which form a part hereof and show, by way of illustration, specific exemplary embodiments. These embodiments are disclosed in sufficient detail to enable those skilled in the art to practice the invention. However, embodiments may be implemented in many different forms and should not be construed as being limited to the embodiments set forth herein. The following detailed description is, therefore, not to be taken in a limiting sense in that the scope of the present invention is defined only by the appended claims.

Figure 1:
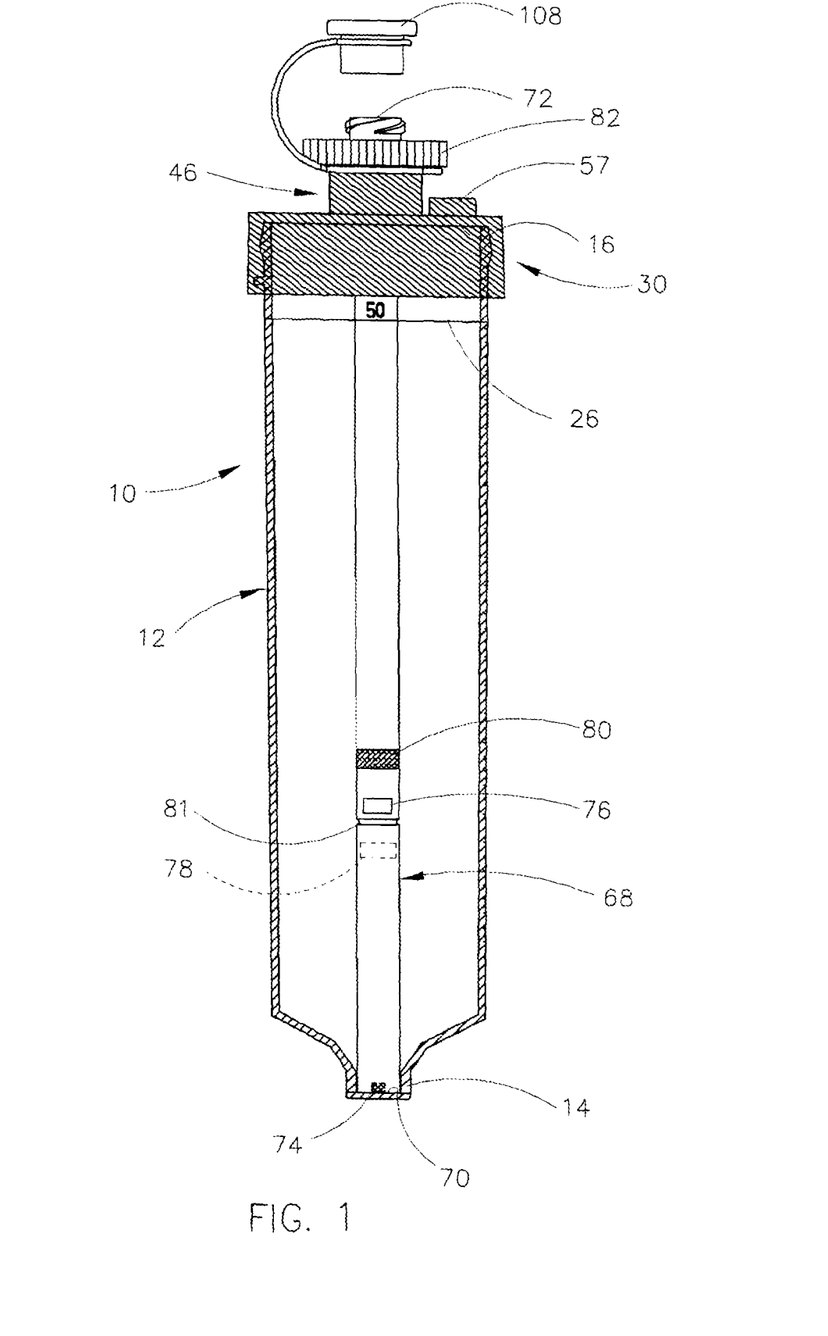
FIG. 1 is a partial sectional view of the centrifuge tube assembly of this invention.
Figure 4:
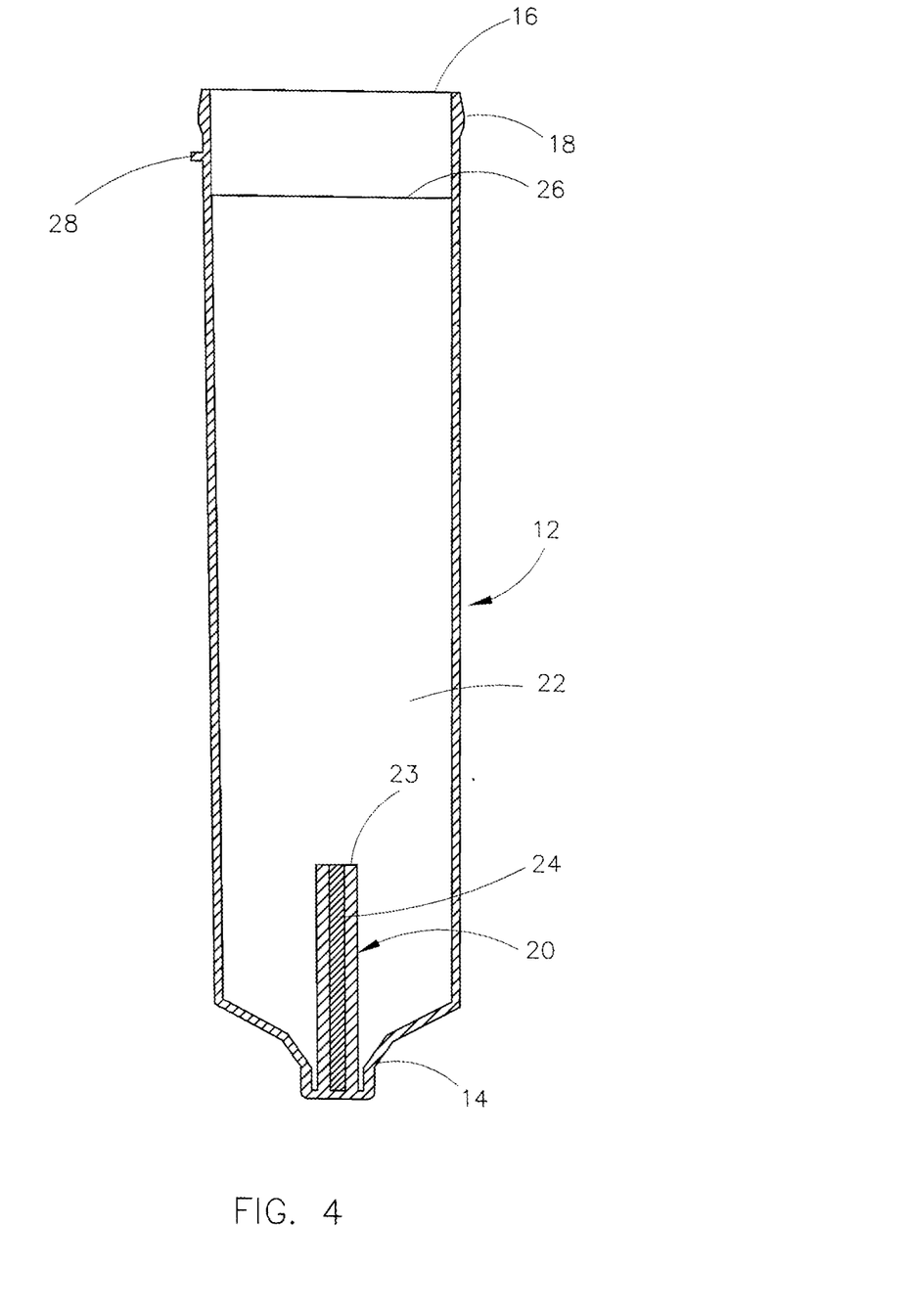
FIG. 4 is a sectional view of the outer containment tube of the centrifuge tube assembly of this invention.

The numeral 10 refers generally to the centrifuge tube assembly of this invention which will be referred to hereinafter as "assembly". Assembly 10 includes an outer containment tube 12 having a tapered and closed lower end 14 and an open upper end 16. The upper outer side of tube 12 has mating geometry in the form of a protruding annular bulge 18. An upstanding cylindrical post 20 is integrally formed with tube 12 and extends upwardly from lower end 14 into the interior 22 of tube 12. For purposes of description, post 20 will be described as having an upper end 23. A vertically disposed keyway or slot 24 is formed in post 20. Tube 12 also has a 50 mm line 26 imprinted thereon below the upper end 16. Tube 12 also has a stop 28 which protrudes laterally from the outer side of tube 12 below the upper end thereof.

Figure 5:
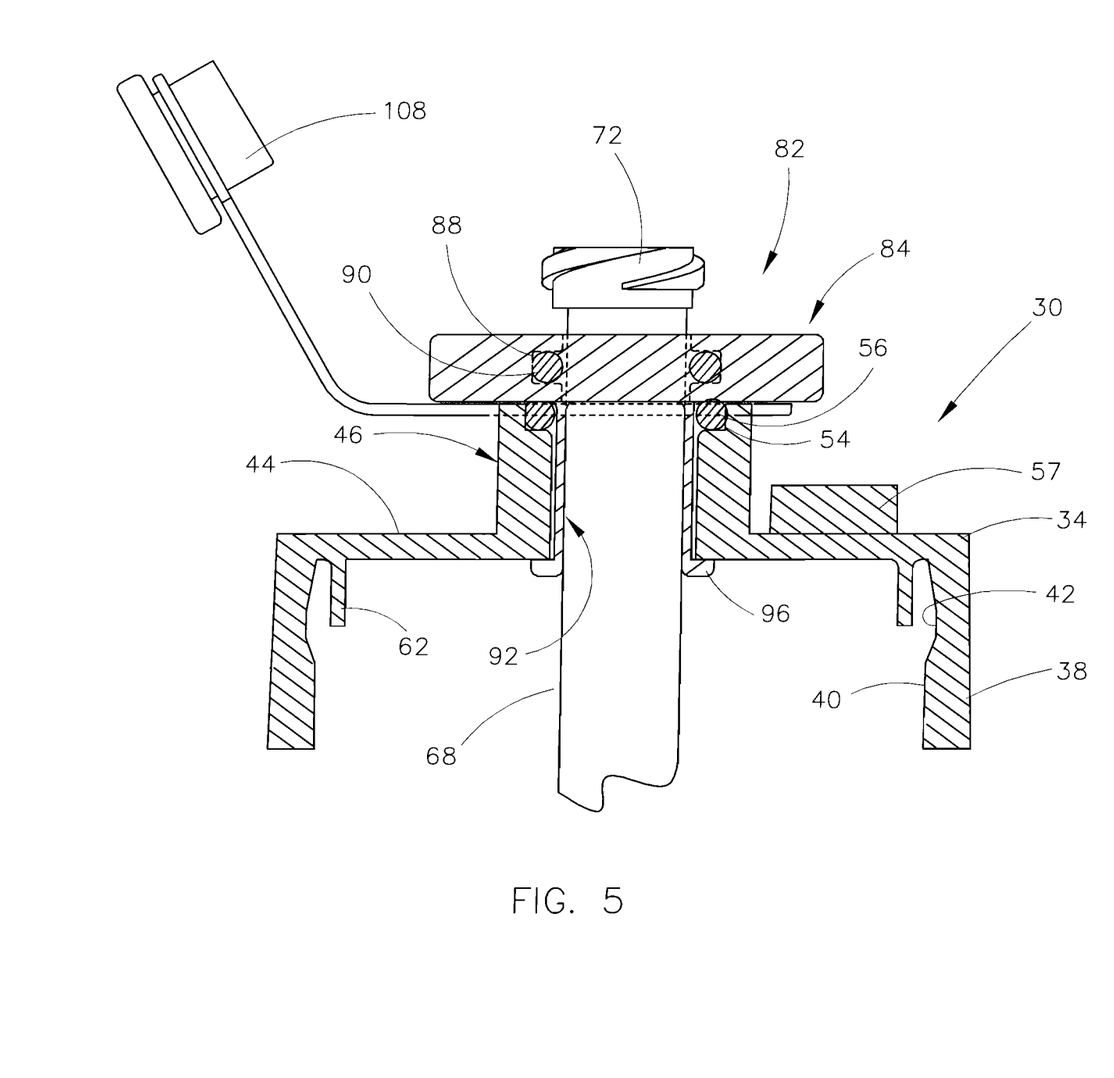
FIG. 5 is a partial sectional view of the cap and inner tube lock and their relationship with the inner tube of the centrifuge tube assembly of this invention.
Figure 6:
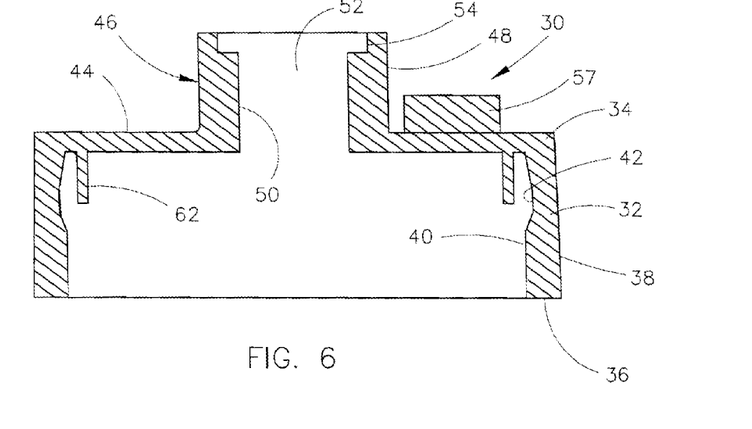
FIG. 6 is a sectional view of the cap of the centrifuge tube assembly of this invention.
Figure 7:
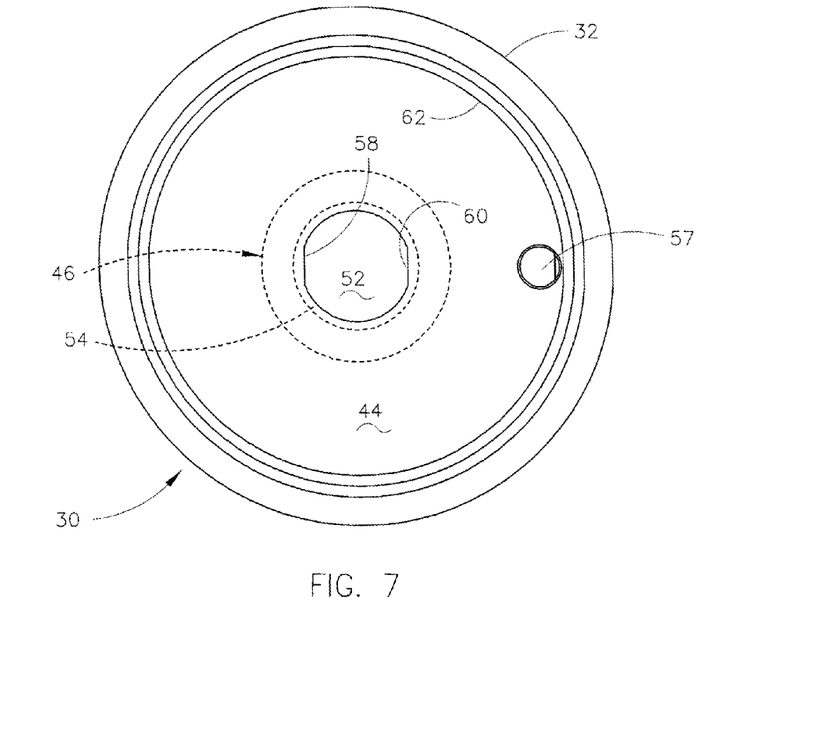
FIG. 7 is a bottom elevational view of the cap of the centrifuge tube assembly of this invention.

Assembly 10 also includes a cup-shaped cap 30 having a cylindrical side wall portion 32 with an upper end 34, a lower end 36, an outer side 38 and an inner side 40. The upper inner side 40 of side wall portion 32 has an annular recessed portion 42 thereon. A horizontally disposed top wall portion 44 extends laterally inwardly from the upper end of side wall portion 32. A cylindrical throat or neck portion 46 extends upwardly from the inner end of top wall portion 44 and has an outer side 48 and an inner side 50 which define a central opening 52. Throat portion 46 has an annular recess or groove 54 formed therein at its upper end which receives an O-ring 56 therein. Top wall portion 44 has a filtered vent port 57 associated therewith. The side walls of central opening 52 have a pair of oppositely disposed chords 58 and 60 formed therein. The underside of top wall portion 44 has an annular wall 62 extending downwardly therefrom inwardly of the annular recessed portion 42.

Figure 2:
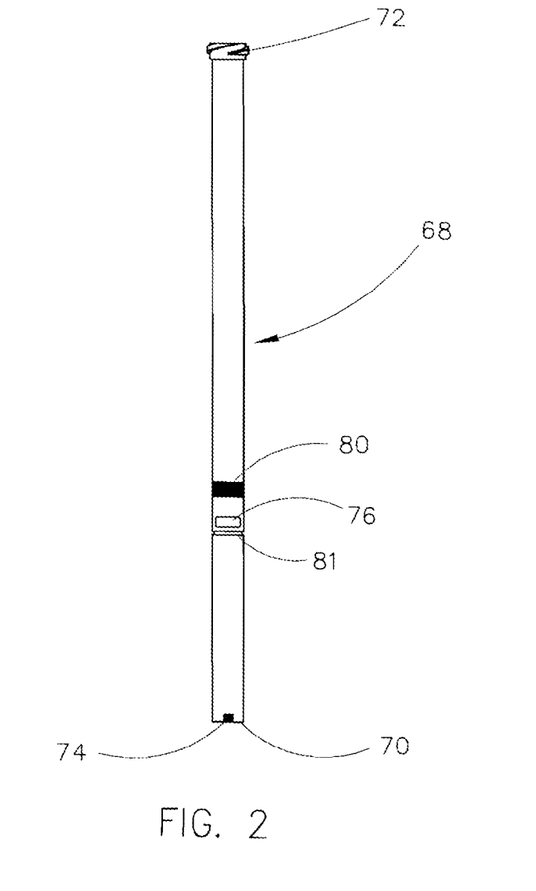
FIG. 2 is a side view of the inner tube of the centrifuge tube assembly of this invention.
Figure 3:
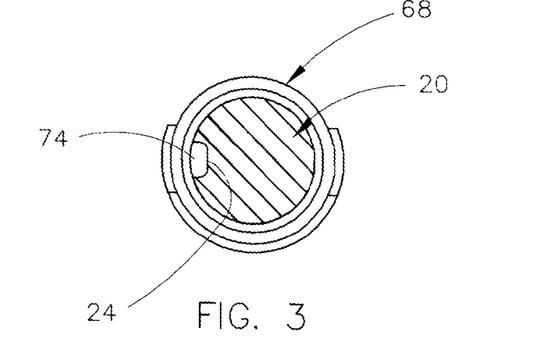
FIG. 3 is a bottom view of the inner tube of the centrifuge tube assembly of this invention with the cylindrical post being shown in section.

The assembly 10 also includes an elongated inner tube 68 having an open lower end 70 and an open upper end 72 in the form of a male luer. Inner tube 68 has an anti-rotation key 74 formed thereon at its lower end which is configured to extend into the keyway 24 of post 20 as will be discussed in detail hereinafter.

Inner tube 68 has an aspiration port 76 formed therein above its lower end. Inner tube 68 also has an inside diameter stop 78 therein just below aspiration port 76. Inner tube 68 also has an imprinted black band 80 thereon above aspiration port 76. Inner tube 68 also has an undercut 81 formed therein below aspiration port 76.

Figure 8:
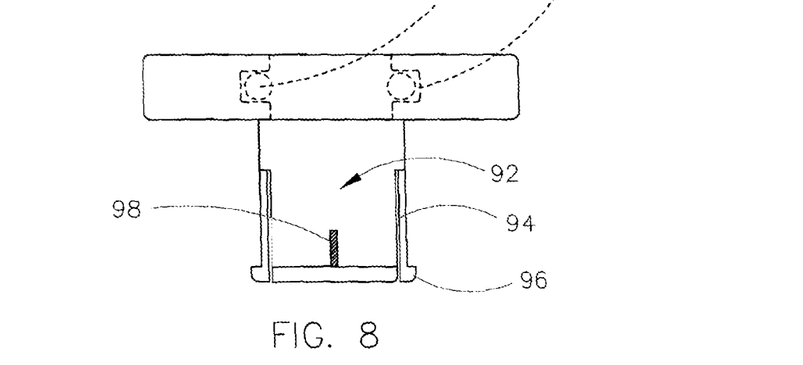
FIG. 8 is a top view of the inner tube lock mechanism of the centrifuge tube assembly of this invention.
Figure 9:
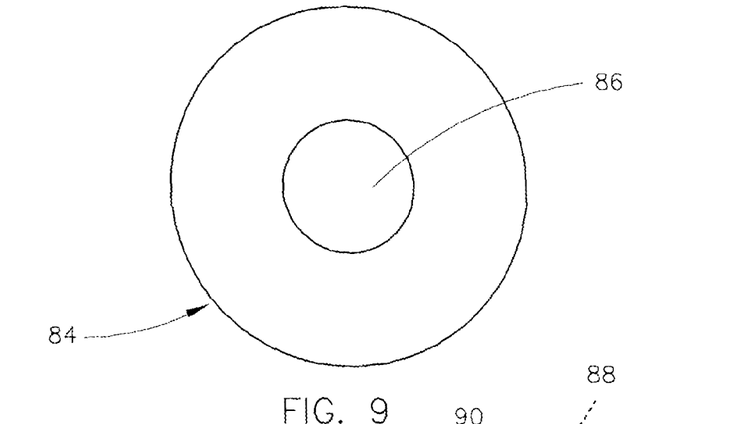
FIG. 9 is a top view of the disc of the inner tube lock mechanism.
Figure 10:
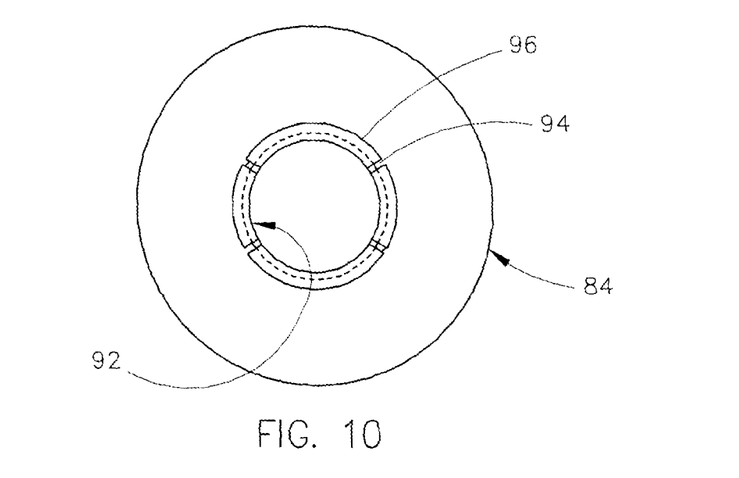
FIG. 10 is a bottom elevational view of the inner tube lock mechanism.

The numeral 82 refers to an inner tube lock assembly. Assembly 82 includes a horizontally disposed and rotatable disc 84 having a central opening 86 extending therebetween. The wall surface around opening 86 has an annular channel 88 formed therein which has an O-ring 90 positioned therein. Assembly 82 includes a generally cylindrical and hollow body portion 92 which extends downwardly from disc 84. Body portion 92 has four radially spaced-apart and vertically disposed slits 94 formed therein. The lower end of body portion 92 has four radially spaced-apart inner tube lock tabs 96 extending horizontally outwardly therefrom. Body portion 92 has a pair of 180 degree spaced-apart chord tabs 98 formed therewith which extend outwardly from the outer surface of body portion 92. The O-ring 56 embraces body portion 92 above the slits 94.

The inner tube lock assembly 82 is mounted on and in the cap 30 as follows. The inner tube lock assembly 82 is initially rotated with respect to cap 30 so that the chord tabs 98 are located at 90 degrees from the chords 58 and 60 in central opening 52 of throat 46 of cap 30. The body portion 92 of assembly 82 is then pushed downwardly through the central opening 52 in throat 46 of cap 30. The four slits 94 permit the body portion 92 to slightly collapse or spring out so that the body portion 92 may be completely inserted downwardly in the central opening 52 and then spring back so that the four inner tube lock tabs 96 are positioned below the top wall portion 44 of cap 30 as seen in FIG. 5.

The inner tube 68 is inserted downwardly into the tube 12 by inserting the inner tube 68 downwardly through central opening 86 in disc 84, and through body portion 92. The inner tube 68 is then rotated until the anti-rotation key 74 is aligned with keyway 24 of post 20. The inner tube 68 is then pushed downwardly until the lower end of inner tube 68 is positioned at the lower end of post 20.

Figure 11:
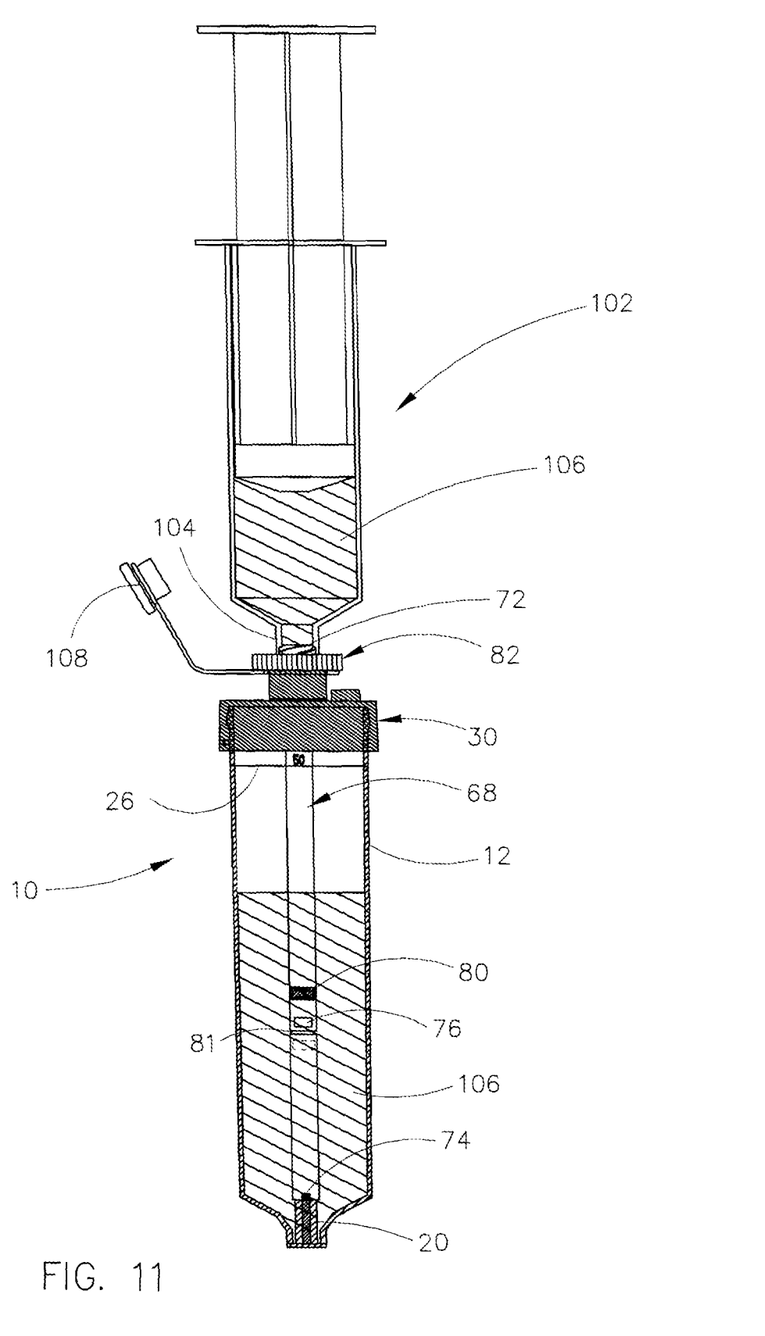
FIG. 11 is a partial sectional view illustrating the orientation and inter-connection between the outer containment tube, the inner tube and a syringe connected to a male luer at the upper end of the inner tube.
Figure 12:
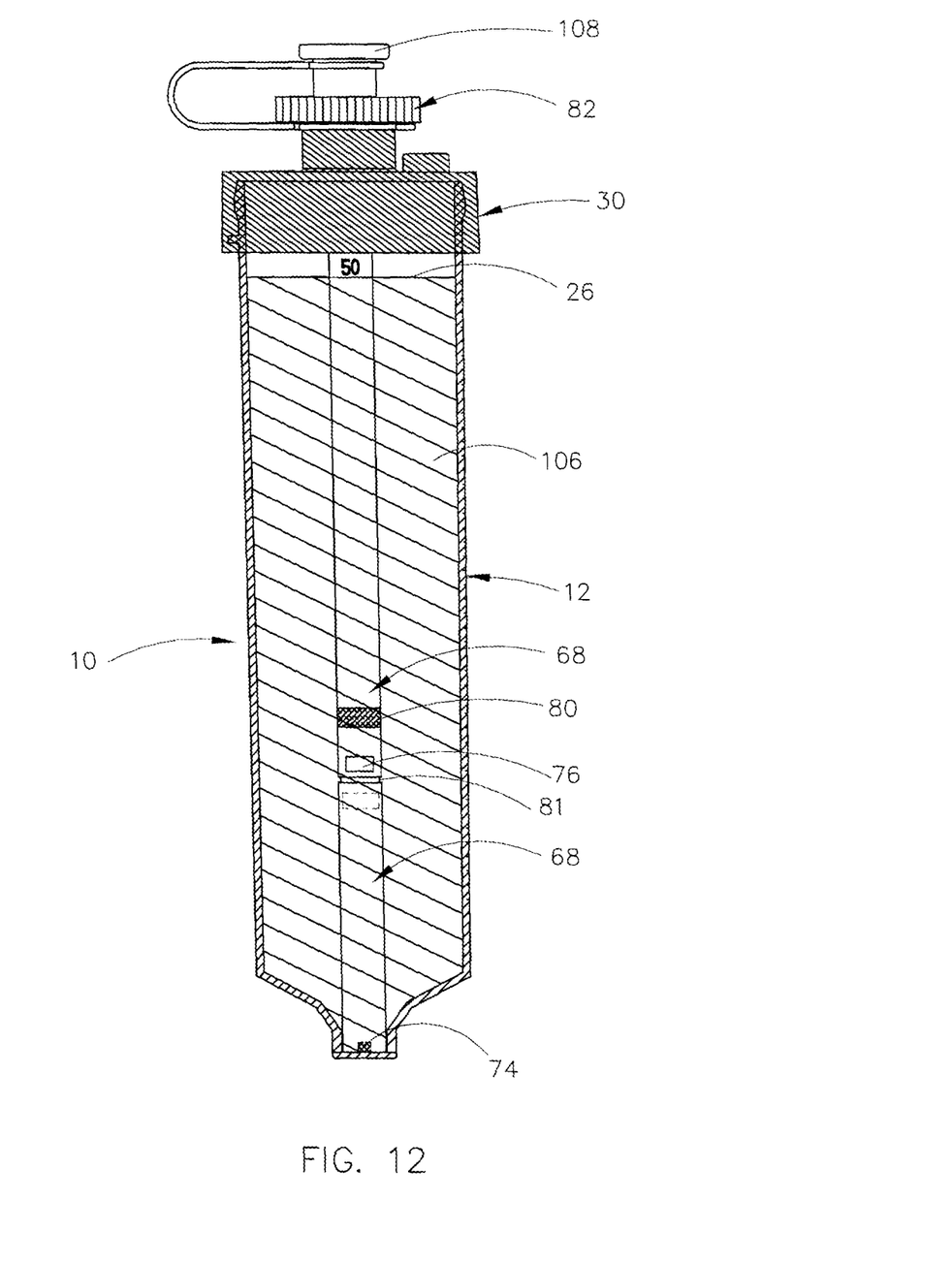
FIG. 12 is a sectional view of the centrifuge tube assembly and which illustrates a biohazard safety luer cap secured to the upper end of the inner tube during centrifugation.

The numeral 102 refers to a 60 ml blood sample syringe having a female luer 104 which is configured to be threaded onto the male luer 72 at the upper end of inner tube 68. The syringe 102 is filled with a blood sample mixture 106 containing a mixture of 41 ml whole blood and 9 ml of ACD-A. The blood sample mixture 106 is dispensed from syringe 102 into the outer tube 12 to the 50 ml fill line 26. The 60 ml syringe 102 is then unthreaded from the inner tube male luer 72. A biohazard safety luer cap 108 is then threaded onto the inner tube male luer 72.

Figure 13:
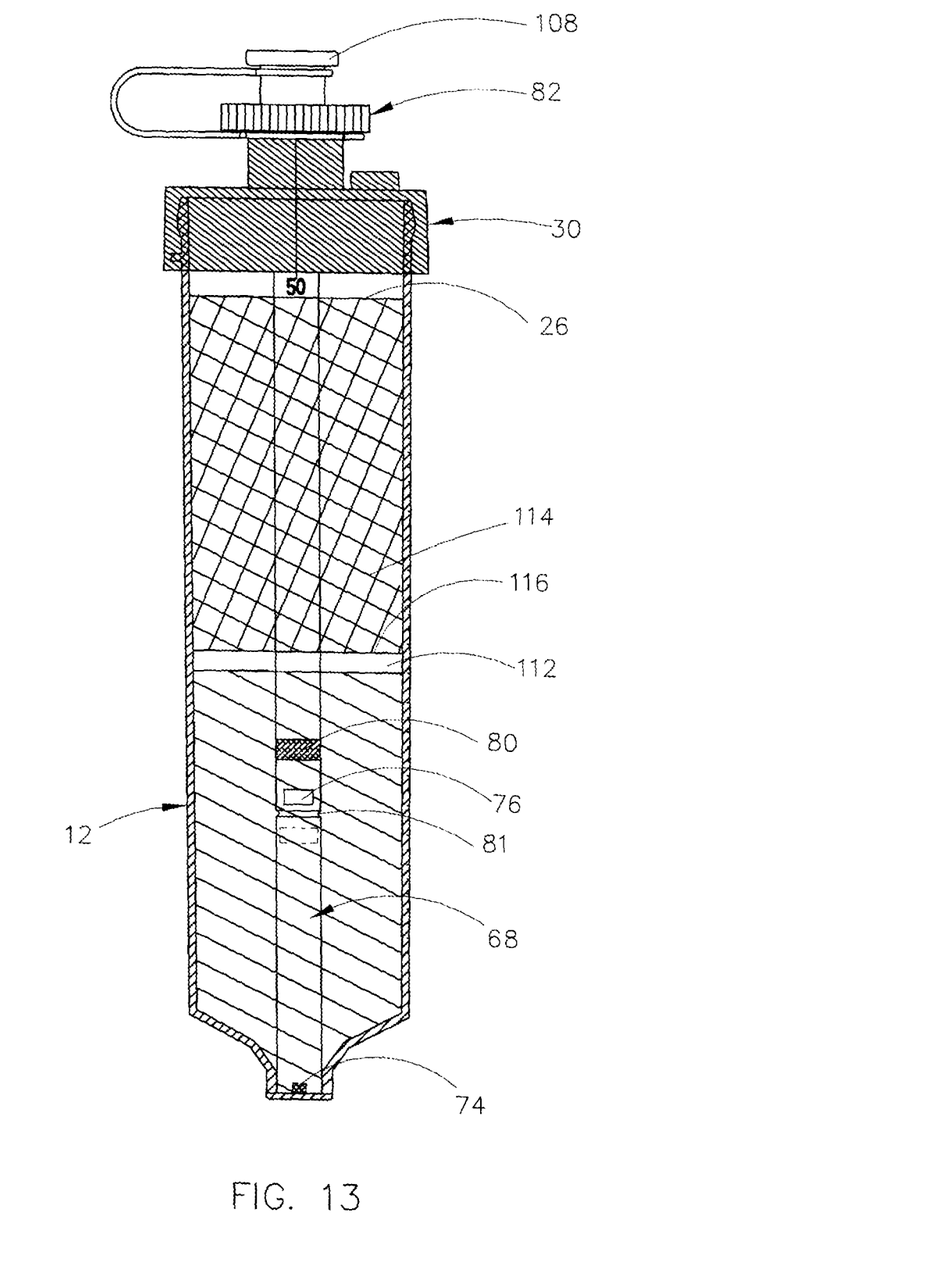
FIG. 13 is a sectional view of the transparent outer containment tube which permits a person to view the component's demarcation of plasma, red cells and buffy coat.
Figure 14:
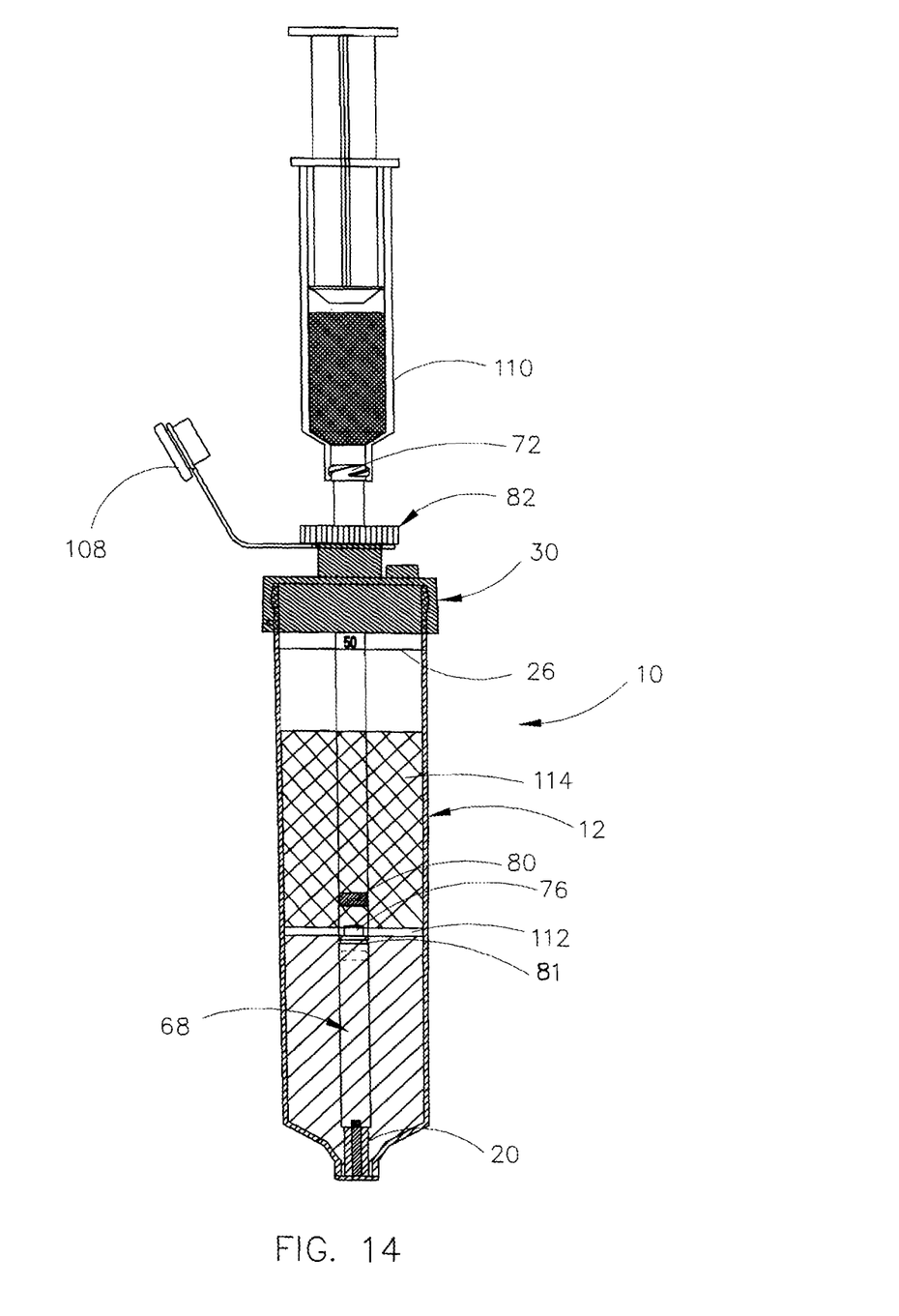
FIG. 14 is a partial sectional view illustrating the inner tube of the assembly being vertically raised for connection to a syringe.

The assembly is then placed in a centrifuge and spun at 1900 rcf for approximately 8.5 minutes. The assembly is then removed from the centrifuge. The technician, holding the device in a vertical position, removes the female luer cap 108 from the male luer 72 and threads a 10 ml syringe 110 onto the inner tube male luer 72 and visually locates the buffy coat layer 112. The technician slowly raises the inner tube 78 by grasping the male luer 72 and syringe connection until the lower (trailing) edge of the colored band 80 is visible and the buffy coat layer 112 and plasma 114 fractionation line 116. The technician then locks the inner tube lock assembly 82 by rotating the lock assembly 82 ninety degrees so that the chord tabs 98 engage the chords 58 and 60 which causes the body portion 92 to squeeze the inner tube 68 to lock the inner tube in the desired vertical position. The technician aspirates the desired volume into the syringe 110.

Figure 15:
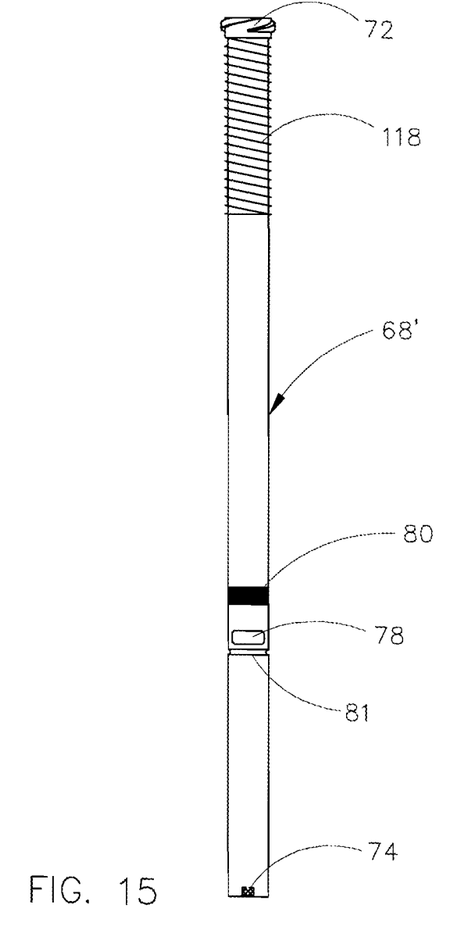
FIG. 15 is a side view of a modified inner tube with the cylindrical post being shown in section.
Figure 16:
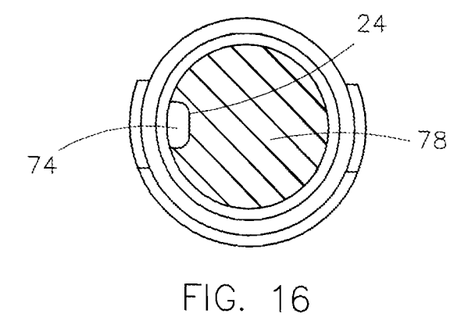
FIG. 16 is a bottom view of the modified inner tube.

FIG. 15 illustrates an optional design for the inner tube 68 and which is designated the numeral 68'. The only difference between inner tube 68' and inner tube 68 is that inner tube 68' has an externally threaded portion 118 below the male luer 72. All other features and functions of inner tube 68' are the same as inner tube 68.

Figure 17:
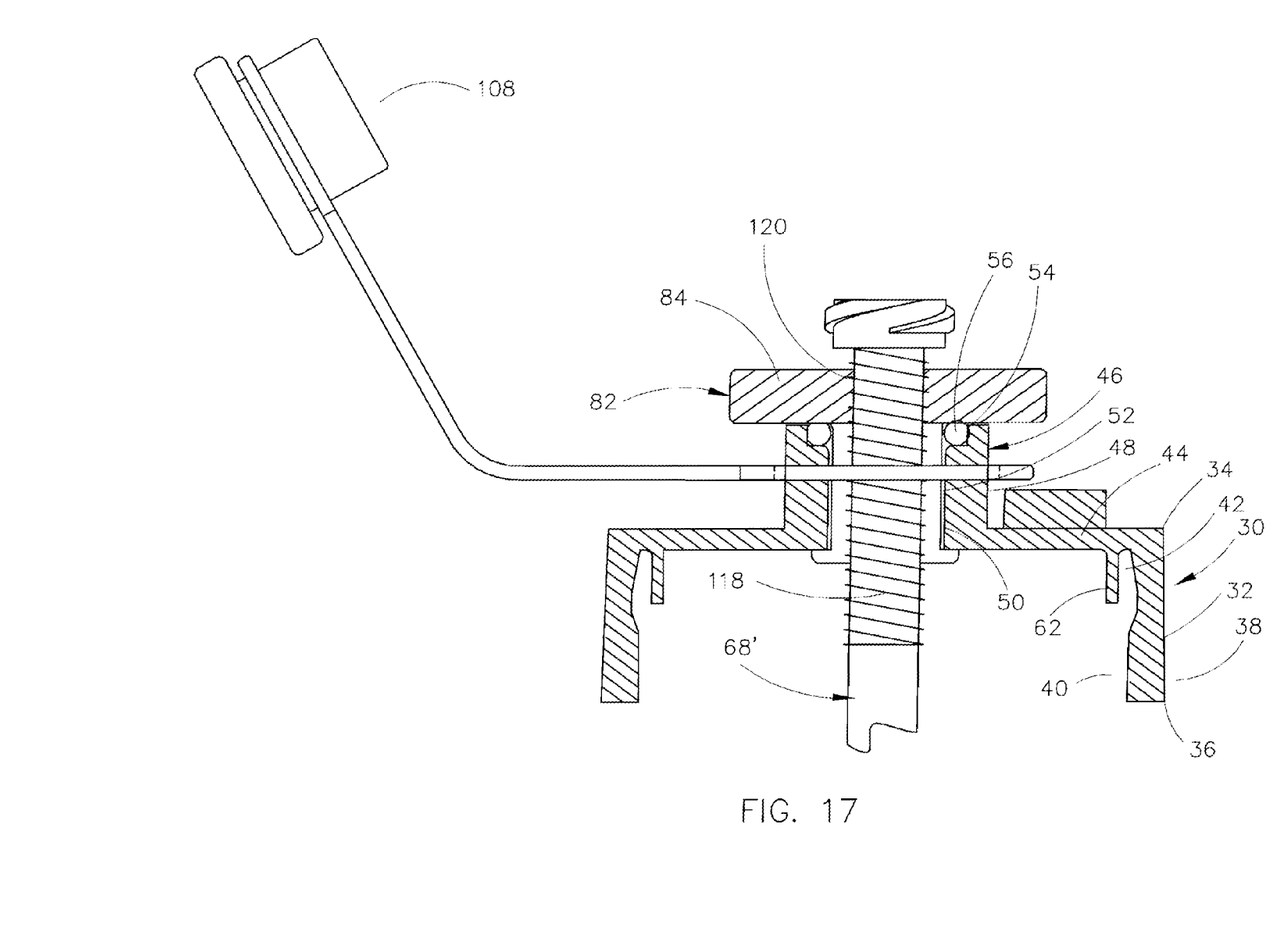
FIG. 17 is a partial sectional view which shows the modified form of the inner tube and a modified inner tube adjuster.
Figure 18:
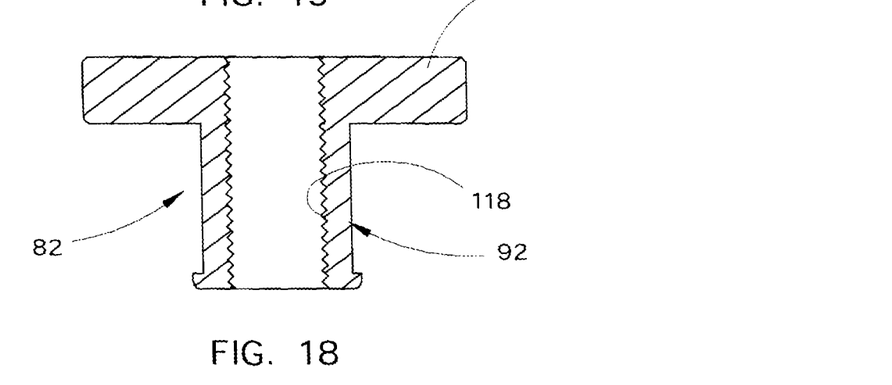
FIG. 18 is a sectional view of the body portion of the modified inner tube lock.
Figure 19:
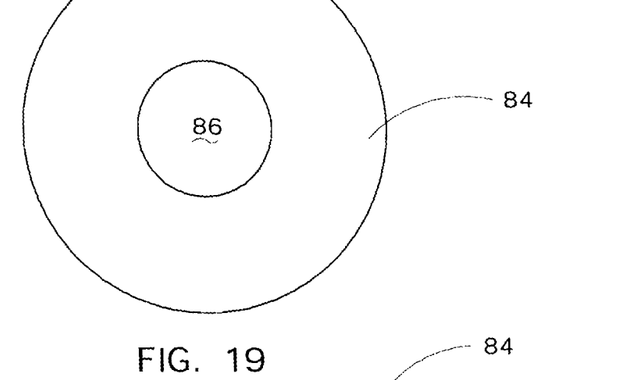
FIG. 19 is a top view of the locking disc of the inner tube lock of FIG. 18.
Figure 20:
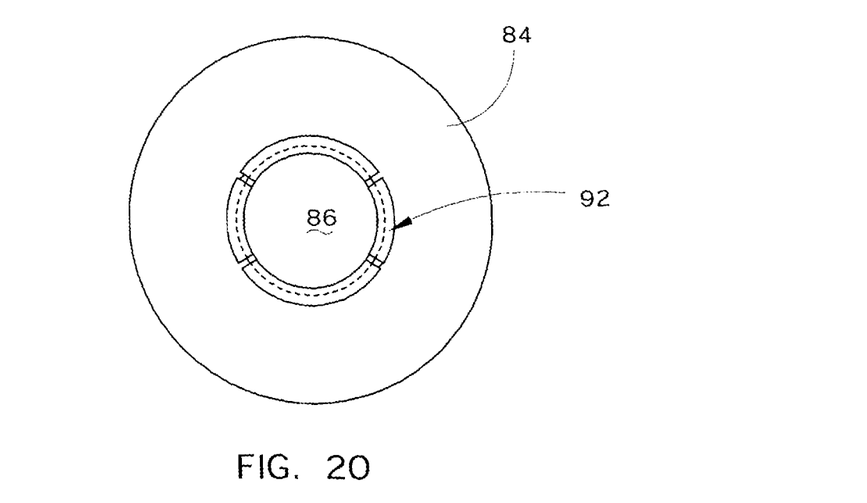
FIG. 20 is a bottom elevational view of the inner tube lock of FIG. 17.

FIG. 17 illustrates a modified method of vertically moving the inner tube 68'. Disc 84 and body portion 92 have internally threads 120 which threadably receive the threaded portion 118 of inner tube 68'. The O-ring 56 provides a seal at the mating point of the modified inner tube 68' and the threaded disc 84. The O-ring 56 provides a tactical feedback and surface fraction between the threaded disc 82 and the cap 30 to secure the inner tube 68' in place.

Thus it can be seen that an improved centrifuge tube assembly has been provided. The assembly of this invention serves both as a collection vessel and a tube for the centrifugation of fluids into their discrete components. Further, the assembly of this invention includes a single port at the top of the device which may be used to fill and aspirate fluid, pre-centrifugation and post-centrifugation therefrom. It can also be seen that the device of this invention enables a clinician to have complete control over the concentration and volume of the end product. A further advantage of the assembly of this invention is that it provides the most cost effective solution specifically designed for the concentration of platelets, stem cells or adipose tissue. Yet another advantage of the invention is that it has the ability to extract the blood component of choice after centrifugation.

Thus it can be seen that the invention accomplishes at least all of its stated objectives.

Although the invention has been described in language that is specific to certain structures and methodological steps, it is to be understood that the invention defined in the appended claims is not necessarily limited to the specific structures and/or steps described. Rather, the specific aspects and steps are described as forms of implementing the claimed invention. Since many embodiments of the invention can be practiced without departing from the spirit and scope of the invention, the invention resides in the claims hereinafter appended.

I claim:

1. A centrifuge tube assembly, comprising:
an elongated and vertically disposed outer containment tube having an open upper end and a closed lower end;
said outer containment tube being comprised of a transparent material;
said outer containment tube having a vertically disposed cylindrical post centrally positioned therein, which has upper and lower ends and which extends upwardly from said lower end thereof;
said cylindrical post having an elongated and vertically disposed keyway formed therein which extends inwardly thereinto between said lower and upper ends thereof;
an elongated and vertically disposed inner tube, having an open lower end and an open upper end, positioned in said outer containment tube;
said lower end of said inner tube being vertically slidably mounted on said cylindrical post;
said inner tube having an alignment key at said lower end thereof which is slidably received by said keyway in said cylindrical post to prevent rotation of said inner tube with respect to said cylindrical post and said outer confinement tube;
said inner tube having an aspiration port formed therein above said lower end thereof;
said inner tube having an imprinted band thereon above said aspiration port;
said outer containment tube having an imprinted millimeter line thereon below said upper end thereof;
a cup-shaped cap selectively removably mounted on said upper end of said outer containment tube;
said cap having a filtered vent port which is in communication with the interior of said outer containment tube;
said inner tube selectively slidably extending upwardly through said cap whereby said upper end of said inner tube is positioned above said cap;
a seal means in said cap between said cap and said inner tube;
a locking assembly associated with said cap for selectively locking said inner tube in various vertical positions with respect to said outer containment tube;
said upper end of said inner tube having a male luer thereon; and a female luer cap for selective engagement with said male luer to close said male luer.

2. The centrifuge tube assembly of claim 1 further including an O-ring in said cap which frictionally embraces said inner tube to yieldably prevent vertical movement of said tube prior to locking assembly being locked.

3. A centrifuge tube assembly, comprising:

an elongated and vertically disposed outer containment tube having an open upper end and a closed lower end;

said outer containment tube being comprised of a transparent material;

said outer containment tube having a vertically disposed cylindrical post centrally positioned therein, which has upper and lower ends and which extends upwardly from said lower end thereof;

said cylindrical post having an elongated and vertically disposed keyway formed therein which extends inwardly thereinto between said lower and upper ends thereof;

an elongated and vertically disposed inner tube, having an open lower end and an open upper end, positioned in said outer containment tube;

said lower end of said inner tube being vertically slidably mounted on said cylindrical post;

said inner tube having an alignment key therein at said lower end thereof which is slidably received by said keyway in said cylindrical post to prevent rotation of said inner tube with respect to said cylindrical post and said outer confinement tube;

said inner tube having an aspiration port formed therein above said lower end thereof;

said inner tube having an imprinted band thereon above said aspiration port;

said outer tube having an imprinted 50 millimeter line thereon below said upper end thereof;

said inner tube having an externally threaded portion below said male luer;

a cup-shaped cap selectively removably mounted on said upper end of said outer containment tube;

said cap having a filtered vent port which is in communication with the interior of said outer containment tube;

said inner tube selectively slidably extending upwardly through said cap whereby said upper end of said inner tube is positioned above said cap;

a seal means in said cap between said cap and said inner tube;

an inner tube adjuster rotatably mounted on said cap;

said inner tube adjuster having an internally threaded opening extending therethrough which threadably receives said externally threaded portion of said inner tube whereby rotation of said inner tube adjuster in one direction causes said inner tube to be vertically moved upwardly with respect to said outer containment tube and whereby rotation of said inner tube adjuster in an opposite direction causes said inner tube to be vertically moved downwardly with respect to said outer containment tube;

said upper end of said inner tube having a male luer thereon; and a female luer cap for selective engagement with said male luer to close said male luer.

4. A method for the aspiration, separation, isolation and extraction of discrete layers in a liquid suspension, comprising the steps of:

providing a vertically disposed transparent outer containment tube having an open upper end, and a closed lower end with the outer containment tube having a vertically disposed post extending upwardly from the lower end thereof;

closing the upper end of said outer containment tube with a cap having a central opening formed therein;

providing a vertically disposed inner tube, having open upper and lower ends and an aspiration port formed therein above said lower end thereof;

inserting said inner tube downwardly through said central opening in said cap so that said lower end of said inner tube is vertically slidably mounted on said post and so that said upper end of said inner tube is disposed above said cap;

placing a predetermined amount of a liquid suspension into said outer containment tube;

closing said open upper end of said inner tube;

placing the outer containment tube, said inner tube and said cap into a centrifuge for a predetermined length of time at a predetermined rotation rate to separate the liquid suspension into discrete layers;

opening the closed upper end of said inner tube;

connecting a syringe to the upper end of said inner tube;

vertically moving said syringe and said inner tube with respect to said outer tube whereby said aspiration port is placed in communication with one of the discrete layers; and aspirating an amount of the discrete layer into the syringe.

5. The method of claim 4 further including the step of locking said inner tube in position when said inner tube has been vertically moved to be in communication with the said one discrete layer.

6. The method of claim 5 further including the step of vertically moving said inner tube so that said aspiration port communicates with another discrete layer after the said one discrete layer has been aspirated.

* * * * *